US006084124A

United States Patent [19]
Slaugh et al.

[11] Patent Number: 6,084,124
[45] Date of Patent: Jul. 4, 2000

[54] METHOD TO PREPARE α-β UNSATURATED CARBOXYLIC ACIDS FROM EPOXIDES USING A COBALT AND TIN CATALYST SYSTEM

[75] Inventors: Lynn Henry Slaugh, Houston; Thomas Clayton Forschner, Richmond, both of Tex.

[73] Assignee: Shell Oil Company, Houston, Tex.

[21] Appl. No.: 09/244,922

[22] Filed: Feb. 4, 1999

Related U.S. Application Data

[60] Provisional application No. 60/073,930, Feb. 6, 1998.
[51] Int. Cl.[7] .......................... C07C 51/10; C07C 51/145; C07C 51/12
[52] U.S. Cl. ......................... 562/517; 562/518; 562/519; 562/523; 562/531; 562/532; 562/533; 562/534; 562/537; 562/544; 562/545; 562/546
[58] Field of Search ...................................... 562/546, 545, 562/544, 534, 533, 532, 531, 523, 519, 518, 517, 537

[56] References Cited

U.S. PATENT DOCUMENTS

| | | | |
|---|---|---|---|
| 3,892,794 | 7/1975 | Grasselli et al. | 260/465.3 |
| 4,209,467 | 6/1980 | Kojima et al. | 260/340.7 |
| 5,310,948 | 5/1994 | Drent et al. | 549/328 |

*Primary Examiner*—Gary Geist
*Assistant Examiner*—Robert W. Deemie
*Attorney, Agent, or Firm*—Del S. Christensen

[57] ABSTRACT

The present invention is a method to produce an unsaturated carboxylic acid which includes the steps of: providing an epoxy compound; contacting the epoxy compound with carbon monoxide in the presence of a catalytically effective amount of a catalyst system comprising tin and cobalt under conditions effective for carbonylation of the epoxy; and recovering a α-β unsaturated carboxylic acid product. The preferred epoxy is ethylene oxide which is reacted to acrylic acid by the method of the present invention.

21 Claims, No Drawings

METHOD TO PREPARE α-β UNSATURATED CARBOXYLIC ACIDS FROM EPOXIDES USING A COBALT AND TIN CATALYST SYSTEM

This application claims the benefit of U.S. Provisional Application Ser. No. 60/073,930 filed Feb. 6, 1998, the entire disclosure of which is hereby incorporated by reference.

FIELD OF THE INVENTION

The invention relates to a method to produce α-β unsaturated acids by carbonylation of an epoxy.

BACKGROUND TO THE INVENTION

U.S. Pat. No. 5,310,948 discloses a method to produce α-β unsaturated carboxylic acids from epoxies by carbonylation and then dehydration of a β-propiolactone intermediate. The catalyst system used includes a source of cobalt and a hydroxyl-substituted pyidine compound.

Aldehydes are produced according to U.S. Pat. No. 4,209,467, by hydroformylation of olefins using a catalyst which is a reaction product of a cobalt carbonyl compound and a hydroxy substituted pyridine compound.

A promoted and reduced combination of molybdenum oxide and antimony oxide is disclosed in U.S. Pat. No. 3,892,794 as being a useful catalyst for oxidation of olefins to unsaturated aldehydes and acids. Tin is disclosed as an effective promoter for this catalyst system. Although the carboxylic acids can be made directly from the olefin feed stock, conversion and yields of the carboxylic acids are not high.

It would therefore be desirable to have a process to produce α-β unsaturated carboxylic acids wherein the yields and conversions are high, and wherein the process is a one stage process. It is therefore an object of the present invention to provide such a process.

SUMMARY OF THE INVENTION

This and other objects are accomplished by a method comprising the steps of: providing an epoxy compound; contacting the epoxy compound with carbon monoxide in the presence of a catalytically effective amount of a catalyst system comprising tin and cobalt; and recovering a α-β unsaturated carboxylic acid product. The reaction readily takes place in a temperature range of 60° C. to 130° C., and preferably the epoxy and catalyst are combined in a solvent such as an alcohol, toluene, chlorobenzene or ether. When an unsaturated acid having two to five carbons is produced, and a water insoluble solvent is used, the α-β unsaturated carboxylic acid product can be recovered by extraction of the acid with water followed by separation of the acid from the water by distillation.

DESCRIPTION OF A PREFERRED EMBODIMENT

The preferred epoxy of the present invention is ethylene oxide, which results in a product of acrylic acid by the method of the present invention. The propylene oxide is also a commercially significant starting material for the present invention, resulting in methacrylic acid product.

The tin and cobalt of the present invention can be provided in any form which is soluble in acceptable solvents for the epoxide and products. For example, carboxylates, alkoxides, halides, oxylates, sulfates, alkyl, tetrafluoroborates, phosphates, carbonates, and mixtures thereof may be used. The form of the cobalt and tin is not critical. The molar ratio of epoxide to cobalt is preferably between about 5 and about 10,000, and more preferably between about 20 and about 1000. The ratio of cobalt to tin is preferably between about 0.1 and about 10 and more preferably between about 0.5 and about 3. The tin component has a valence of either +2 or +4.

The catalyzed reaction of the present invention preferably is performed in a temperature range between about 60° C. and about 130° C., more preferably in the range of 80° C. to 110° C. and most preferably in the range of 80° C. to 90° C. The total pressure for the reaction of the present invention is preferably at least 200 psig, more preferably in the range of about 200 to 2000 psig, and most preferably in the range of about 500 to 1200 psig.

The catalyst of the present invention is preferably provided in a solvent which may be either a water soluble solvent or a water insoluble solvent, so long as it is a solvent for the reactants and catalyst system. Solvents such as cylcohexane, toluene, benzene, halogenated aromatics, alcohols, and ethers may be utilized. When a solvent is utilized which is not water soluble, the acid product of the present invention may be recovered by extraction into a water phase, and then distillation from the water. The organic solvent, which preferably contains the catalyst components, can then be readily recycled (preferably after being dehydrated). If a solvent is utilized which is water soluble, the carboxylic acid product can be removed by distillation from the reaction mixture. The catalyst system is preferably contacted with the epoxy and carbon monoxide with mixing to provide contact between the components. The contacting of the epoxy, carbon monoxide and catalyst system may be performed continuously or as a batch operation. The continuous contacting may be accomplished in, for example, a stirred tank reactor.

EXAMPLES

Four examples of the invention and one comparative example (without the tin component) were performed. For each example, an autoclave in a nitrogen purged drybox was loaded with solvent, dicobalt octacarbonyl (0.34 mmoles) and, for each example except the comparative example, one mmole of tin 2-ethylhexanoate was added. The solvent was a combination of methyl alcohol ("MeOH") and methyl-t-butyl ether("MTBE"). The sealed, air-free autoclave was pressured to 500 psig with carbon monoxide and then heated to the reaction temperature. The contents of the autoclave were mechanically stirred. Ethylene oxide (43 mmoles) was then injected under carbon monoxide pressure. The autoclave pressure was then raised to 1200 psig with carbon monoxide. After heating and stirring for six hours, the autoclave was cooled in an ice bath, vented to atmospheric pressure, opened, and 20 ml of deairated distilled water was added. After stirring the contents for a few minutes, stirring was discontinued, and an organic layer and an aqueous layer separated. The organic layer contained most of the catalyst. The aqueous layer contained acrylic acid product. The amount of acrylic acid, the amount of methyl 3-hydroxypropionate and the amount of other unidentified hydrocarbons were determined by GC. The TABLE below contains the results. In the TABLE "M3-H" is methyl 3-hydroxypropionate. The acrylic acid, M3-H, and "other" are based on the amount of ethylene oxide that was converted, and the ethylene oxide conversion ("CONV.") is based on the amount of ethylene oxide charged to the autoclave.

TABLE

| Example No. | Solvent, ml | Temp. °C. | Conv., % | Acrylic acid, % | M3-H, % | other, % |
|---|---|---|---|---|---|---|
| 1 | MeOH,5 MTBE, 27 | 90. | 31. | 57.4 | 28.4 | 14.2 |
| 2 | MeOH,5 MTBE, 27 | 100 | 42. | 71.2 | 6.8 | 22.0 |
| 3 | MeOH,5 MTBE, 27 | 120 | 5.4 | 89.9 | 7.8 | 2.3 |
| 4 | MeOH, 32 | 90 | 58.9 | 66.8 | 13.7 | 19.5 |
| C1 | MTBE, 27 MeOH,5 | 90 | 3. | 0. | 100. | 0. |

From the TABLE, it can be seen that presence of the tin compound is essential for conversion of the epoxide directly to the acid.

We claim:

1. A method for producing a α-β unsaturated carboxylic acid the method comprising the steps of:
   providing an epoxy compound;
   contacting the epoxy compound with carbon monoxide in the presence of a catalytically effective amount of a catalyst system comprising tin and cobalt under conditions effective for carbonylation of the epoxy; and
   recovering a α-β unsaturated carboxylic acid product.

2. The method of claim 1 wherein the conditions effective for carbonylation include a temperature in the range of 60° C. to 130° C.

3. The method of claim 2 wherein the conditions effective for carbonylation include a temperature in the range of 80° C. to 110° C.

4. The method of claim 3 wherein the conditions effective for carbonylation include a temperature in the range of 80° C. to 90° C.

5. The method of claim 1 wherein the conditions effective for carbonylation include a pressure of at least 200 psig.

6. The method of claim 5 wherein the conditions effective for carbonlyation include a pressure in the range of 200 to 2000 psig.

7. The method of claim 6 wherein the conditions effective for carbonlyation include a pressure in the range of 500 to 1200 psig.

8. The method of claim 1 wherein the epoxy compound is ethylene oxide.

9. The method of claim 1 wherein the epoxy compound is propylene oxide.

10. The method of claim 1 wherein the contacting of the epoxy compound with carbon monoxide is performed in a solvent selected from the group comprising an ether, aromatic, halogenated aromatic, alcohol, and mixtures thereof.

11. The method of claim 1 wherein the tin component has a tin valence selected from the group consisting of +2 and +4.

12. The method of claim 1 wherein the contacting of the epoxy compound with carbon monoxide is performed in a solvent that is not water soluble and the α-β unsaturated carboxylic acid is one which has from two to five carbon atoms.

13. The method of claim 12 wherein recovering a α-β unsaturated carboxylic acid product is accomplished by: adding water to the reaction mixture; separating the water from the solvent; and removing the α-β unsaturated carboxylic acid from the water.

14. The method of claim 8 wherein the conditions effective for carbonylation include a temperature in the range of 80° C. to 110° C., and the carbon monoxide partial pressure in the range of 500 to 1200 psi.

15. The method of claim 14 wherein the tin component has a tin valence of 2.

16. The method of claim 14 wherein the contacting of the epoxy compound with carbon monoxide is performed in a solvent that is not water soluble.

17. The method of claim 16 wherein recovering a α-β unsaturated carboxylic acid product is accomplished by: adding water to the reaction mixture; separating the water from the solvent; and removing the α-β unsaturated carboxylic acid from the water.

18. The method of claim 1 wherein the molar ratio of epoxide to cobalt is between about 5 and about 10,000.

19. The method of claim 18 wherein the molar ratio of epoxide to cobalt is between about 20 and about 1000.

20. The method of claim 18 wherein the molar ratio of cobalt to tin is between about 0.1 and about 10.

21. The method of claim 19 wherein the molar ratio of cobalt to tin is between about 0.5 and about 3.

* * * * *